United States Patent
Kagawa (10) Patent No.: US 11,559,193 B2
(45) Date of Patent: Jan. 24, 2023

(54) MEDICAL CONTROL DEVICE AND ENDOSCOPE SYSTEM

(71) Applicant: Sony Olympus Medical Solutions Inc., Tokyo (JP)

(72) Inventor: Ryohei Kagawa, Tokyo (JP)

(73) Assignee: SONY OLYMPUS MEDICAL SOLUTIONS INC., Tokyo (JP)

( * ) Notice: Subject to any disclaimer, the term of this patent is extended or adjusted under 35 U.S.C. 154(b) by 365 days.

(21) Appl. No.: 16/729,524

(22) Filed: Dec. 30, 2019

(65) Prior Publication Data

US 2020/0297199 A1 Sep. 24, 2020

(30) Foreign Application Priority Data

Mar. 22, 2019 (JP) .............................. JP2019-055705

(51) Int. Cl.
*A61B 1/045* (2006.01)
*A61B 1/00* (2006.01)
*A61B 1/06* (2006.01)
*A61B 1/05* (2006.01)

(52) U.S. Cl.
CPC .......... *A61B 1/045* (2013.01); *A61B 1/00006* (2013.01); *A61B 1/00009* (2013.01); *A61B 1/00013* (2013.01); *A61B 1/051* (2013.01); *A61B 1/0661* (2013.01)

(58) Field of Classification Search
CPC ................................................... H04N 5/3535
See application file for complete search history.

(56) References Cited

U.S. PATENT DOCUMENTS

| | | | | |
|---|---|---|---|---|
| 8,767,095 B2* | 7/2014 | Fukushima | .......... | H04N 5/2256 348/222.1 |
| 8,785,833 B2* | 7/2014 | Yabe | ...................... | G03B 15/05 600/109 |
| 2013/0201315 A1* | 8/2013 | Takei | .................. | H04N 5/23254 348/77 |
| 2013/0300849 A1* | 11/2013 | Ono | .................... | A61B 1/00006 348/68 |
| 2013/0307951 A1* | 11/2013 | Ono | ...................... | H04N 5/2354 348/68 |

(Continued)

FOREIGN PATENT DOCUMENTS

| | | |
|---|---|---|
| JP | 5948512 B2 | 7/2016 |
| WO | 2015/194415 A1 | 12/2015 |
| WO | 2017/047166 A1 | 3/2017 |

*Primary Examiner* — Anh Tuan T Nguyen
*Assistant Examiner* — Jae Woo
(74) *Attorney, Agent, or Firm* — Xsensus LLP (57) ABSTRACT

A medical control device includes: a light source controller configured to modulate pulsed light by changing a crest value of a pulsed current and emit the pulsed light a plurality of times from the light source in one frame; an imaging controller configured to cause an image sensor to sequentially generate a pixel signal at a specific frame rate; and an image processor configured to use a pixel signal obtained by multiplying the pixel signal for specific one frame from each pixel of a specific horizontal line by a ratio of an amount of exposure of specific pulsed light made in the specific one frame to a total exposure amount obtained by adding each exposure amount of all of the pulsed lights exposing the specific horizontal line within the specific one frame including an illumination period of the specific pulsed light.

9 Claims, 8 Drawing Sheets

(56) References Cited

U.S. PATENT DOCUMENTS

| | | | |
|---|---|---|---|
| 2014/0014820 A1* | 1/2014 | Yabe | G02B 23/2484 |
| | | | 250/208.1 |
| 2014/0198249 A1* | 7/2014 | Tanaka | H04N 5/2354 |
| | | | 348/370 |
| 2014/0203170 A1* | 7/2014 | Ono | H04N 5/2354 |
| | | | 250/208.1 |
| 2014/0316196 A1* | 10/2014 | Wichern | A61B 1/042 |
| | | | 600/109 |
| 2014/0364690 A1* | 12/2014 | Seto | A61B 1/045 |
| | | | 348/70 |
| 2015/0124124 A1* | 5/2015 | Maeyama | H04N 5/343 |
| | | | 348/235 |
| 2016/0066769 A1* | 3/2016 | Hashimoto | A61B 1/06 |
| | | | 600/109 |
| 2016/0120398 A1* | 5/2016 | Kubo | A61B 1/0638 |
| | | | 348/68 |
| 2016/0345812 A1* | 12/2016 | Ogasawara | A61B 1/042 |
| 2016/0360948 A1* | 12/2016 | Mizuno | H04N 5/2353 |
| 2017/0064178 A1* | 3/2017 | Kagawa | H04N 5/2353 |
| 2017/0238791 A1* | 8/2017 | Kagawa | H04N 5/3532 |
| 2018/0140173 A1* | 5/2018 | Nishio | H04N 5/2256 |
| 2019/0008372 A1* | 1/2019 | Tanaka | H04N 7/18 |
| 2020/0297199 A1* | 9/2020 | Kagawa | A61B 1/045 |
| 2020/0404146 A1* | 12/2020 | Talbert | A61B 1/045 |
| 2021/0037176 A1* | 2/2021 | Sato | G10L 25/48 |

* cited by examiner

MEDICAL CONTROL DEVICE AND ENDOSCOPE SYSTEM

This application claims priority from Japanese Application No. 2019-055705, filed on Mar. 22, 2019, the contents of which are incorporated by reference herein in its entirety.

BACKGROUND

The present disclosure relates to a medical control device and an endoscope system.

In a medical field, known in the related art is an endoscope system for observing vocal cords by sequentially emitting pulsed light toward the vocal cords in synchronization with a vibration frequency of the vocal cords and imaging the pulsed light reflected from the vocal cords with an image sensor (see, for example, JP 5948512 B2).

In an endoscope system described in JP 5948512 B2, in order to reduce brightness variations within one frame or between successive frames due to a difference between a frame period of an image sensor and a light emission period of pulsed light and generate an image suitable for observation, processing described below is executed.

Specifically, in the endoscope system, a pixel signal output from an image sensor is operated with a specific arithmetic expression, thereby generating a pseudo pixel signal (pixel signal during illumination) corresponding to a pixel signal when all pixels of the image sensor are exposed during an illumination period of pulsed light.

SUMMARY

However, in the endoscope system described in JP 5948512 B2, when pulsed light is modulated by changing a crest value (current value) of a pulsed current supplied to a light source that emits the pulsed light according to the supplied pulsed current, if operated with the specific arithmetic expression described above, an appropriate pseudo pixel signal may not be generated. In brief, fluctuations in brightness other than ones targeted through light modulation occur. This makes it difficult to reduce variations in brightness within one frame or between successive frames, and thus generate an image suitable for observation.

There is a need for a medical control device and an endoscope system that may generate an image suitable for observation.

According to one aspect of the present disclosure, there is provided a medical control device including: a light source controller configured to control operations of a light source configured to emit pulsed light according to a pulsed current, the light source controller being configured to modulate the pulsed light by changing a crest value of the pulsed current and emit the pulsed light a plurality of times from the light source in one frame; an imaging controller configured to control operations of an image sensor including a plurality of pixels configured to receive light from an object illuminated with the pulsed light and generate a pixel signal, the imaging controller being configured to cause the image sensor to sequentially generate the pixel signal at a specific frame rate; and an image processor configured to generate, from the pixel signal, a pseudo pixel signal corresponding to a pixel signal when the pixels are exposed in an illumination period of the specific pulsed light, the image processor being configured to use, when generating the pseudo pixel signal, for a specific horizontal line among horizontal lines of the pixels, a pixel signal obtained by multiplying the pixel signal for specific one frame from each pixel of the specific horizontal line by a ratio of an amount of exposure of the specific pulsed light made in the specific one frame to a total exposure amount obtained by adding each exposure amount of all of the pulsed lights exposing the specific horizontal line within the specific one frame including an illumination period of the specific pulsed light, wherein the exposure amount is a value defined by a pulse width and the crest value of the pulsed current.

DETAILED DESCRIPTION

Hereinafter, embodiments for carrying out the present disclosure (hereinafter referred to as embodiments) will be described with reference to the drawings. The present disclosure is not limited by embodiments described below. Additionally, in descriptions of the drawings, identical sections are denoted by identical reference numerals.

First Embodiment

Schematic Configuration of Endoscope System

Figure 1:
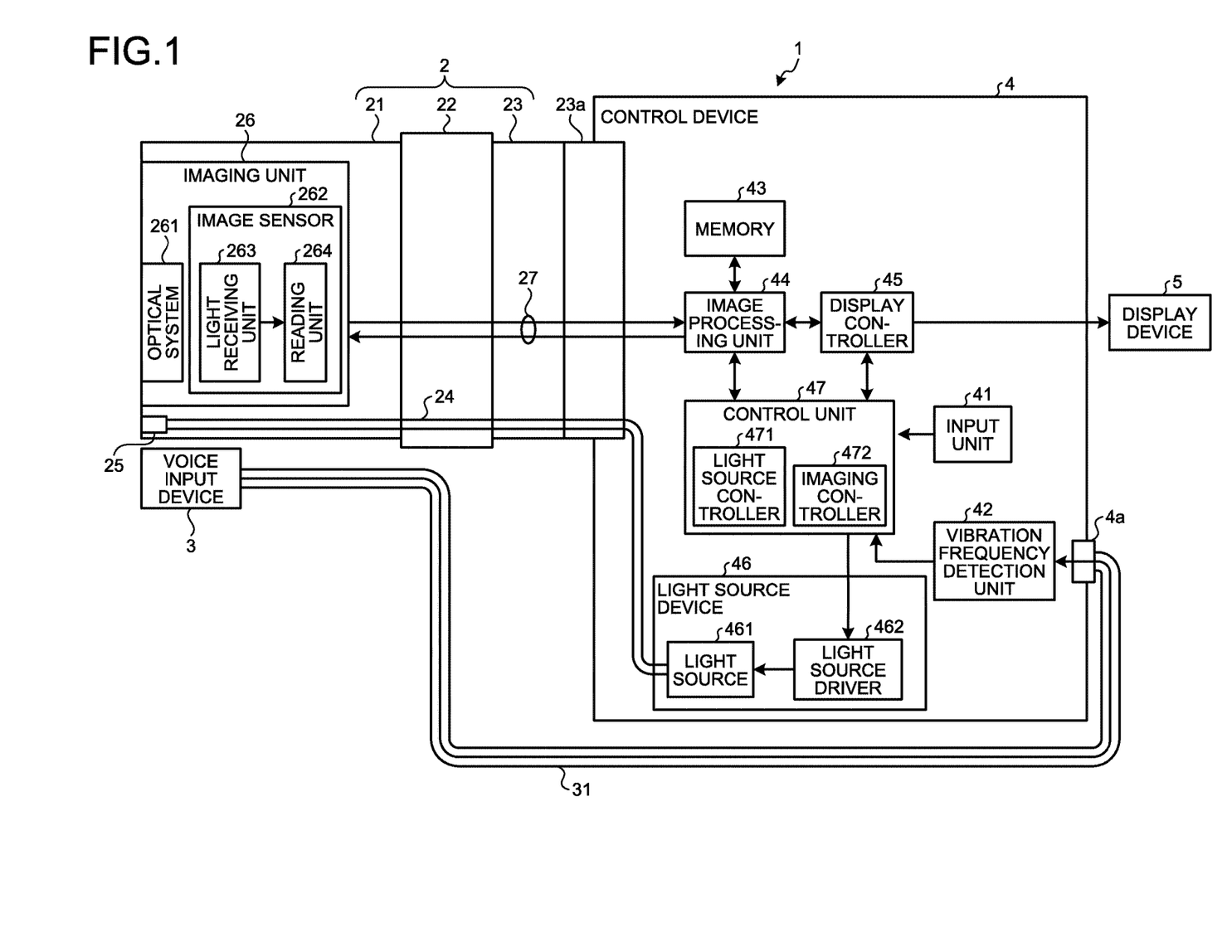
FIG. 1 is a block diagram illustrating an endoscope system according to a first embodiment.

FIG. 1 is a block diagram illustrating an endoscope system 1 according to a first embodiment.

The endoscope system 1 is used in a medical field and is a stroboscopic endoscope system for observing vocal cords as an object. The endoscope system 1 includes, as illustrated in FIG. 1, an endoscope 2, a voice input device 3, a control device 4, and a display device 5.

The endoscope 2 captures an object image from vocal cords. The endoscope 2 includes, as illustrated in FIG. 1, an insertion unit 21, an operating unit 22, and a universal cord 23.

The insertion unit 21 has an elongated shape. As illustrated in FIG. 1, an illumination fiber of a light guide 24 is inserted into the insertion unit 21. At a distal end portion of the insertion unit 21, an illumination lens 25 is provided to face an emission end of the light guide 24. Pulsed light emitted from the light guide 24 is applied to vocal cords via the illumination lens 25.

In addition, at the distal end portion of the insertion unit 21, an imaging unit 26 is provided as illustrated in FIG. 1.

The imaging unit 26 is a part that captures light (object image) applied to vocal cords via the illumination lens 25 and reflected by the vocal cords into the insertion unit 21 and captures the object image. The imaging unit 26 includes, as illustrated in FIG. 1, an optical system 261 and an image sensor 262.

The optical system 261 includes one or a plurality of lenses and captures an object image from vocal cords into the insertion unit 21 to form an image on a light receiving surface of the image sensor 262 (light receiving unit 263).

The image sensor 262 sequentially captures, under control of the control device 4, an object image formed by the optical system 261 at a specific frame rate. The image sensor 262 includes, as illustrated in FIG. 1, the light receiving unit 263 and a reading unit 264.

On the light receiving surface of the light receiving unit 263, a plurality of pixels that receives an object image formed by the optical system 261 and photoelectrically converts the received object image to generate a pixel signal is arranged. The pixels are arranged in a matrix so that a plurality of pixel rows (horizontal lines) including two or more pixels arranged in a horizontal direction is arranged in a vertical direction. Then, the light receiving unit 263 generates a pixel signal representing vocal cords from the object image formed on the light receiving surface.

The reading unit 264 exposes the pixels in the light receiving unit 263 and reads pixel signals from the pixels.

In the first embodiment, the image sensor 262 (the light receiving unit 263 and the reading unit 264) includes a CMOS image sensor, and exposure and reading for each horizontal line are possible. Then, the reading unit 264 performs an imaging operation of exposure and reading from a first horizontal line and generates pixel signals by a rolling shutter system that performs charge reset, exposure, and reading by shifting timing for each horizontal line. Therefore, in the imaging unit 26, even in one imaging period (frame), an exposure timing and a reading timing are different for each horizontal line.

Further, as illustrated in FIG. 1, an electric cable 27 for transmitting a pixel signal and a control signal is inserted into the insertion unit 21. More specifically, the imaging unit 26 generates a pixel signal by the rolling shutter system according to a control signal from the control device 4 via the electric cable 27 and outputs the pixel signal to the control device 4 via the electric cable 27.

The operating unit 22 is connected on a proximal end side of the insertion unit 21 and provided with various types of switches (not illustrated) that accept a user operation by a user such as a doctor. Then, the operating unit 22 outputs an operation signal corresponding to the operation to the control device 4 via the electric cable 27.

The universal cord 23 is a cord extending from the operating unit 22 and provided with the light guide 24, the electric cable 27, and the like. The universal cord 23 is connected, at a proximal end thereof, to the control device 4 by a connector 23a.

The voice input device 3 is, as illustrated in FIG. 1, connected via a cord 31 to a voice input terminal 4a of the control device 4. The voice input device 3 inputs a voice emitted from vocal cords and outputs a voice signal. Then, the voice signal is output via the cord 31 to the control device 4.

The control device 4 corresponds to a medical control device according to the present disclosure. The control device 4 includes a central processing unit (CPU), a field-programmable gate array (FPGA), and the like and comprehensively controls operations of the imaging unit 26 and the display device 5.

A detailed configuration of the control device 4 will be described in "Configuration of control device" described later.

The display device 5 includes a display using liquid crystal, organic electro luminescence (EL), or the like and displays, under the control of the control device 4, an image based on a display image signal from the control device 4.

Configuration of Control Device

Next, the configuration of the control device 4 will be described.

The control device 4 includes, as illustrated in FIG. 1, an input unit 41, a vibration frequency detection unit 42, a memory 43, an image processing unit 44, a display controller 45, a light source device 46, and a control unit 47.

The input unit 41 includes operating devices such as a mouse, a keyboard, and a touch panel and accepts a user operation by a user such as a doctor. Then, the input unit 41 outputs an operation signal corresponding to the user operation to the control unit 47.

The vibration frequency detection unit 42 detects, based on a voice signal output from the voice input device 3, a frequency of a voice (vibration frequency of vocal cords) input to the voice input device 3. Then, the vibration frequency detection unit 42 outputs a detected voice frequency to the control unit 47.

The memory 43 includes, for example, a dynamic random access memory (DRAM). The memory 43 temporarily stores pixel signals for multiple frames sequentially read from the reading unit 264. The memory 43 also temporarily stores pseudo-pixel signals, which will be described later, generated by the image processing unit 44 for multiple frames.

The image processing unit 44 generates, from the pixel signals of the consecutive multiple frames stored in the memory 43, a pseudo pixel signal corresponding to a pixel signal when all the pixels of the light receiving unit 263 are exposed during an illumination period of pulsed light by the light source device 46. In the first embodiment, the image processing unit 44 generates a pseudo pixel signal each for all pulsed lights. The image processing unit 44 may employ a configuration that does not generate a pseudo pixel signal each for all pulsed lights.

Details of a method for generating pseudo pixel signals will be described in "Operations of control device" described later.

Further, the image processing unit 44 subjects pixel signals of the pixels read by the reading unit 264 to predetermined image processing. For example, the image processing unit 44 subjects pixel signals to image processings including optical black subtraction processing, white balance (WB) adjustment processing, demosaic processing (when the image sensor 262 includes a Bayer array color filter (not illustrated)), color matrix calculation processing, gamma correction processing, color reproduction processing, edge enhancement processing, and the like.

The display controller 45 generates, as with a method for generating display image signals described in JP 5948512 B2, a display image signal to be displayed on the display device 5 from each pseudo pixel signal in each pulsed light included in a display cycle of the display device 5.

The light source device 46 includes, as illustrated in FIG. 1, a light source 461 and a light source driver 462. In the first embodiment, the light source device 46 is, but not limited to, built in the control device 4 and may be independent of the control device 4.

The light source 461 includes, for example, a white light emitting diode (LED) and emits pulsed light according to a supplied pulsed current. Pulsed light emitted from the light source 461 is applied to vocal cords through the light guide 24 and the illumination lens 25.

The light source driver 462 supplies, under control of the control unit 47, a pulsed current to the light source 461.

The control unit 47 includes, for example, a CPU and an FPGA and controls operations of the imaging unit 26 and the display device 5 as well as controls operations of the entire control device 4. The control unit 47 includes, as illustrated in FIG. 1, a light source controller 471 and an imaging controller 472.

Functions of the light source controller 471 and the imaging controller 472 will be described in "Operations of control device" described later.

Operations of Control Device

Next, operations of the control device 4 described above will be described.

The light source controller 471 causes the light source 461 to emit pulsed light so as to synchronize with a frequency of a voice emitted from an object of vocal cords detected by the vibration frequency detection unit 42.

The imaging controller 472 controls exposure at a specific frame rate by the rolling shutter system that sequentially starts exposure of the image sensor 262 in one frame period for each horizontal line and sequentially reads for each horizontal line after a predetermined period (so-called shutter speed) has elapsed from the start of exposure.

Figure 2:
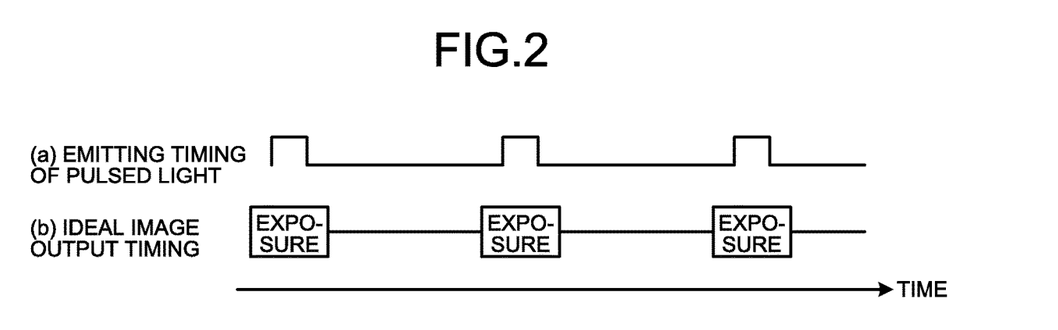
FIG. 2 is a time chart illustrating a relationship between an emitting timing of pulsed light and an ideal image output timing in an imaging unit.

FIG. 2 is a time chart illustrating a relationship between an emitting timing of pulsed light and an ideal image output timing in the imaging unit 26.

Here, as illustrated in FIG. 2, when each emitting timing of pulsed light of the light source 461 in the light source 461 ((a) of FIG. 2) coincides with an exposure timing of the image sensor 262 ((b) of FIG. 2), no variations in brightness occur among a plurality of output images.

In the first embodiment, the light source controller 471 controls operations of the light source 461 so that a light emission period of the light source 461 is shorter than a frame period of the image sensor 262.

Hereinafter, the emitting timing of pulsed light by the light source 461 and exposure and reading timings by the reading unit 264 will be described with reference to FIG. 3.

Figure 3:
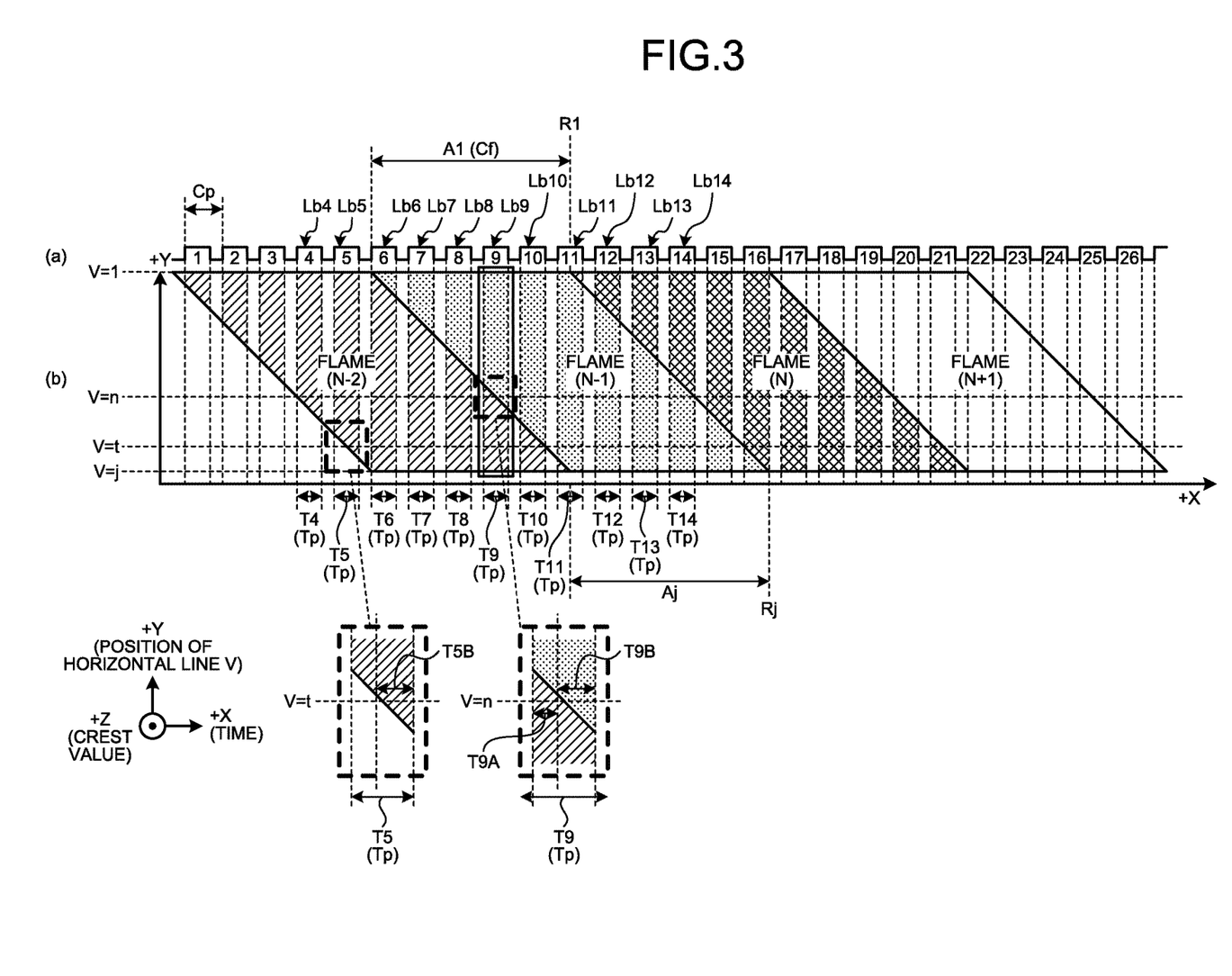
FIG. 3 is a time chart illustrating an emitting timing of pulsed light and an exposure and a reading timings by a reading unit.

FIG. 3 is a diagram for explaining the emitting timing of pulsed light and the exposure and the reading timings by the reading unit 264. Specifically, (a) of FIG. 3 is a timing chart illustrating the emitting timing of pulsed light emitted from the light source 461. (b) of FIG. 3 is a time chart illustrating the exposure and the reading timings for the pixels by the reading unit 264. In (b) of FIG. 3, an XYZ orthogonal coordinate system is used, time is indicated on an X axis, positions of horizontal lines V (V is an integer. V=1, . . . , n, . . . , t, . . . , and j) on the pixels are indicated on a Y axis, and a crest value of a pulsed current supplied to the light source 461 (exposure intensity of pulsed light to a pixel (current value)) is indicated on a Z axis.

The light source 461 emits, under the control of the light source controller 471, as illustrated in (a) of FIG. 3, pulsed light for each light emission period Cp shorter than a frame period Cf of the image sensor 242.

In addition, the imaging unit 26 generates, under control of the imaging controller 472, pixel signals by the rolling shutter system that changes the exposure and the reading timings for each horizontal line V. Therefore, even for pixel signals in an identical frame, an exposure period and the reading timing differ for each horizontal line V. For example, as illustrated in (b) of FIG. 3, for pixels on a first horizontal line 1 in a frame (N−1), the reading unit 264 reads a pixel signal at time R1 after exposure in a period A1. Further, the reading unit 264 exposes and reads pixels on the subsequent horizontal lines V while shifting timings for each horizontal line V in a time direction. Then, pixels on a last horizontal line j are exposed in a period Aj and a pixel signal is read at time Rj. Thus, pixel signals D (N−1) in the frame (N−1) are generated by sequential exposure on each horizontal line V from the first horizontal line 1 to the last horizontal line j and by sequential reading of the pixel signals on the horizontal lines V from the first line during a period from time R1 to time Rj. Pixel signals D (N−2) in a frame (N−2), pixel signals D (N) in a frame (N), and pixel signals D (N+1) in a frame (N+1) are also generated by being read similarly.

From the above, in the first embodiment, in any exposure period on the horizontal lines V, pulsed light is illuminated multiple times, and pixels on each horizontal line V are subjected to multiple exposure. Then, the image processing unit 44 generates pseudo pixel signals considering that some horizontal lines V overlap in reading timing and illumination period of pulsed light and that pixels on each horizontal line V are subjected to multiple exposure.

Hereinafter, a case where the light source controller 471 does not execute light modulation control of pulsed light emitted from the light source 461 and a case where the light source controller 471 executes the light modulation control will be described in order.

[Case of No Light Modulation Control]

Figure 4:
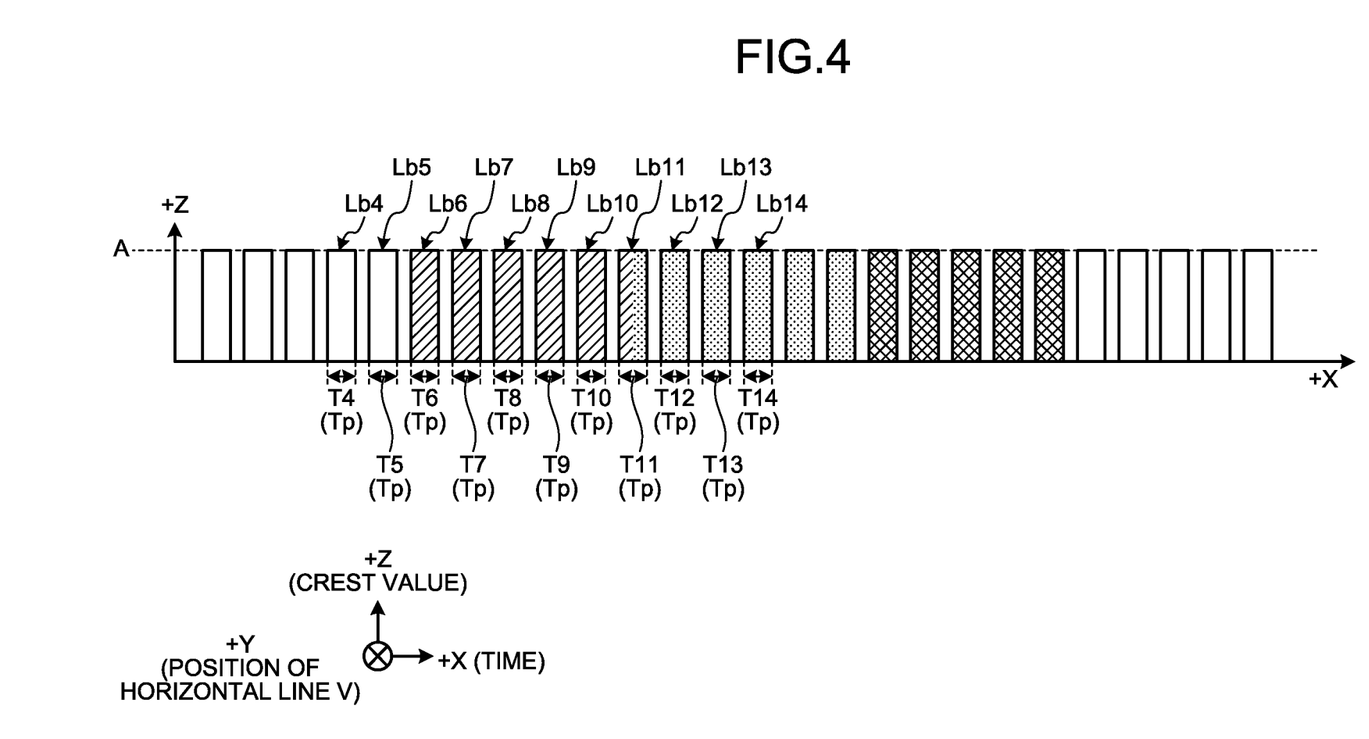
FIG. 4 is a diagram for explaining an exposure amount when light modulation control is not executed.
Figure 5:
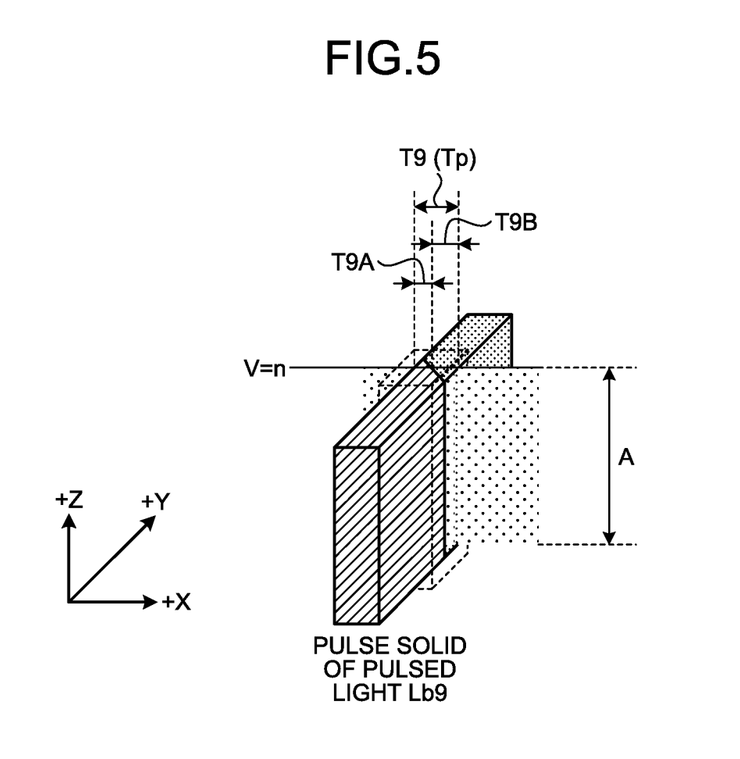
FIG. 5 is a diagram for explaining an exposure amount when light modulation control is not executed.

FIGS. 4 and 5 are diagrams for explaining an exposure amount when light modulation control is not executed. Specifically, FIG. 4 is a diagram when (b) of FIG. 3 is viewed from a −Y axis direction. FIG. 5 is a perspective view in which only a portion of pulsed light Lb9 illustrated in (b) of FIG. 3 (hereinafter referred to as a pulse solid) is extracted, and a pulse solid of the pulsed light Lb9 is viewed from a −Y axis side.

First, a case where the light source controller 471 does not execute light modulation control will be described. In other words, crest values of pulsed currents supplied to the light source 461 are, as illustrated in FIG. 4, uniformly "A". Further, pulse widths (illumination periods) of the pulsed currents supplied to the light source 461 are uniformly "Tp".

Hereinafter, a method for generating pixel signals of overlapping lines constituting pseudo pixel signals and a method for generating pixel signals of non-overlapping lines constituting pseudo pixel signals will be described in order.

Overlapping lines mean horizontal lines V of which a reading timing (hereinafter referred to as a first reading timing) overlaps an illumination period targeted to generate pseudo pixel signals (hereinafter referred to as a target illumination period) (in an example of (b) of FIG. 3, one of the overlapping lines is a horizontal line n). On the other hand, non-overlapping lines mean horizontal lines V except overlapping lines among the horizontal lines V (in the example of (b) of FIG. 3, one of the non-overlapping lines is a horizontal line t). Non-overlapping lines correspond to specific horizontal lines according to the present disclosure.

First, the method for generating pixel signals of overlapping lines constituting pseudo pixel signals will be described.

When generating pseudo pixel signals, the image processing unit 44 uses, for an overlapping line, pixel signals obtained by synthesizing a first corresponding pixel signal derived from a first pixel signal and a second corresponding pixel signal derived from a second pixel signal. The first pixel signal is a pixel signal for one frame of a first frame read from the overlapping line at the first reading timing. The second pixel signal is a pixel signal for one frame of a second frame read from the overlapping line at a second reading timing, one frame after the first reading timing.

Here, the first corresponding pixel signal is a pixel signal obtained by multiplying the first pixel signal by a ratio of an amount of exposure made during the target illumination period in the first frame to a total exposure amount obtained by adding each exposure amount of all pulsed lights that expose the overlapping line in the first frame.

In addition, the second corresponding pixel signal is a pixel signal obtained by multiplying the second pixel signal by a ratio of an amount of exposure made during the target illumination period in the second frame to a total exposure amount obtained by adding each exposure amount of all pulsed lights that expose the overlapping line in the second frame.

Further, the exposure amount described above is defined by a pulse width (illumination period) and a crest value of a pulsed current. More specifically, the exposure amount is an integrated value of illumination period×crest value (corresponding to a cross-sectional area obtained by cutting the pulse solid illustrated in FIG. 5 along an XZ plane (represented by dots in FIG. 5)).

Further more specifically, a case of generating a pseudo pixel signal corresponding to a pixel signal when all pixels of the light receiving unit 263 are exposed with the pulsed light Lb9 will be described in an example of the horizontal line n as an overlapping line.

The image processing unit 44 uses, for an overlapping line of the horizontal line n, a pixel signal obtained by synthesizing a first corresponding pixel signal and a second corresponding pixel signal. The first corresponding pixel signal is derived from a pixel signal of the horizontal line n (first pixel signal) in the pixel signal D (N−2) of the frame (N−2)(first frame) read at a reading timing (first reading timing) overlapping an illumination period (target illumination period) of the pulsed light Lb9. The second corresponding pixel signal is derived from a pixel signal of the horizontal line n (second pixel signal) in the pixel signal D (N−1) of the frame (N−1) (second frame) read at a second reading timing, one frame after the first reading timing.

Here, an exposure period of the horizontal line n of the frame (N−2) includes, in addition to a first half of an illumination period T9 (target illumination period) of the pulsed light Lb9, illumination periods T4 to T8 of pulsed lights Lb4 to Lb8.

Therefore, the first corresponding pixel signal is calculated by formula (1) below. In formula (1), H4 to H9 are crest values of pulsed currents for emitting the pulsed lights Lb4 to Lb9, respectively. A period T9A is, in the frame (N−2), a period in which the illumination period T9 of the pulsed light Lb9 is included in the exposure period of the horizontal line n.

$$\text{first corresponding pixel signal} = \frac{H9*T9A}{H4*T4+H5*T5+H6*T6+H7*T7+H8*T8+H9*T9A} * \text{first pixel signal} \quad (1)$$

Further, an exposure period of the horizontal line n of the frame (N−1) includes, in addition to a latter half of the illumination period T9 of the pulsed light Lb9, the illumination periods T10 to T14 of the pulsed lights Lb10 to Lb14.

Thus, the second corresponding pixel signal is calculated by formula (2) below. In formula (2), H10 to H14 are crest values of pulsed currents for emitting the pulsed lights Lb10 to Lb14, respectively. A period T9B is, in the frame (N−1), a period in which the illumination period T9 of the pulsed light Lb9 is included in the exposure period of the horizontal line n.

$$\text{second corresponding pixel signal} = \frac{H9*T9B}{H9*T9B+H10*T10+H11*T11+H12*T12+H13*T13+H14*T14} * \text{second pixel signal} \quad (2)$$

Then, the image processing unit 44 makes the pixel signal of the horizontal line n, which is an overlapping line constituting the pseudo pixel signal with the pulsed light Lb9, a pixel signal obtained by synthesizing the first corresponding pixel signal calculated by formula (1) and the second corresponding pixel signal calculated by formula (2).

Here, when the light source controller 471 does not execute light modulation control, the crest values H4 to H14 each are uniformly "A". The illumination periods T4 to T14 each are uniformly "Tp". In other words, exposure amounts of the pulsed lights Lb4 to Lb14 (each cross-sectional area (see FIG. 5) obtained by cutting each of pulse solids of the pulsed lights Lb4 to Lb14 along the XZ plane (represented by dots in FIG. 5)) are all identical.

Thus, when the light source controller 471 does not execute light modulation control, formula (1) is developed as formula (3) below. Similarly, formula (2) is developed as formula (4) below.

$$\text{first corresponding pixel signal} = \frac{T9A}{5*Tp+T9A} * \text{first pixel signal} \quad (3)$$

$$\text{second corresponding pixel signal} = \frac{T9B}{T9B+5*Tp} * \text{second pixel signal} \quad (4)$$

In short, when the light source controller 471 does not execute light modulation control, as illustrated in formulae (3) and (4), it is only necessary, in calculating the first and the second corresponding pixel signals, to consider only parameters of time (illumination period) but not crest values.

Next, the method for generating pixel signals of non-overlapping lines constituting pseudo pixel signals will be described.

When generating pseudo pixel signals, the image processing unit 44 uses, for a non-overlapping line, pixel signals obtained by multiplying pixel signals for a specific one frame from each pixel of the non-overlapping line by a ratio of an amount of exposure made during a target illumination period within the specific one frame to a total exposure amount obtained by adding each exposure amount of all pulsed lights exposing the non-overlapping line within the specific one frame including the target illumination period.

More specifically, a case of generating a pseudo pixel signal corresponding to a pixel signal for one frame when all pixels of the light receiving unit 263 are exposed with the pulsed light Lb9 will be described in an example of the horizontal line t as a non-overlapping line.

The image processing unit 44 generates, for a non-overlapping line of the horizontal line t, a pseudo pixel signal based on a pixel signal of the horizontal line t of the pixel signals D (N−2) of the frame (N−2) read at a next reading timing of the illumination period (target illumination period) of the pulsed light Lb9.

Here, an exposure period of the horizontal line t of the frame (N−2) includes, in addition to the illumination period T9 (target illumination period) of the pulsed light Lb9, a latter half of an illumination period T5 of pulsed light Lb5 and the illumination periods T7 to T8 and T10 of the pulsed lights Lb7 to Lb8 and Lb10.

Therefore, the pixel signal of the horizontal line t constituting the pseudo pixel signal with the pulsed light Lb9 is calculated by formula (5) below. In formula (5), a period T5B is, in the frame (N−2), a period in which the illumination period T5 of the pulsed light Lb5 is included in the exposure period of the horizontal line t.

$$\text{pixel signal of horizontal line } t \text{ constituting pseudo pixel signal} \quad (5)$$
$$\text{with pulsed light } Lb9 = \frac{H9*T9}{H5*T5B+H6*T6+H7*T7+H8*T8+H9*T9+H10*T10} *$$
$$(\text{pixel signal of horizontal line } t \text{ of pixel signals } D \ (N-2))$$

Here, when the light source controller 471 does not execute light modulation control, the crest values H5 to H10 each are uniformly "A". The illumination periods T6 to T10 each are uniformly "Tp". More specifically, the exposure amounts of the pulsed lights Lb6 to Lb10 (each cross-sectional area (see FIG. 5) obtained by cutting each of the pulse solids of the pulsed lights Lb6 to Lb10 along the XZ plane (represented by dots in FIG. 5)) are all identical.

Thus, when the light source controller 471 does not execute light modulation control, formula (5) is developed as formula (6) below.

$$\text{pixel signal of horizontal line } t \text{ constituting pseudo} \quad (6)$$
$$\text{pixel signal with pulsed light } Lb9 = \frac{Tp}{T5B+5*Tp} *$$
$$(\text{pixel signal of horizontal line } t \text{ of pixel signals } D \ (N-2))$$

In other words, when the light source controller 471 does not execute light modulation control, as illustrated in formula (6), it is only necessary, in calculating a pixel signal of a non-overlapping line constituting a pseudo pixel signal, to consider only parameters of time (illumination period) but not crest values.

Case of Light Modulation Control

Figure 6:
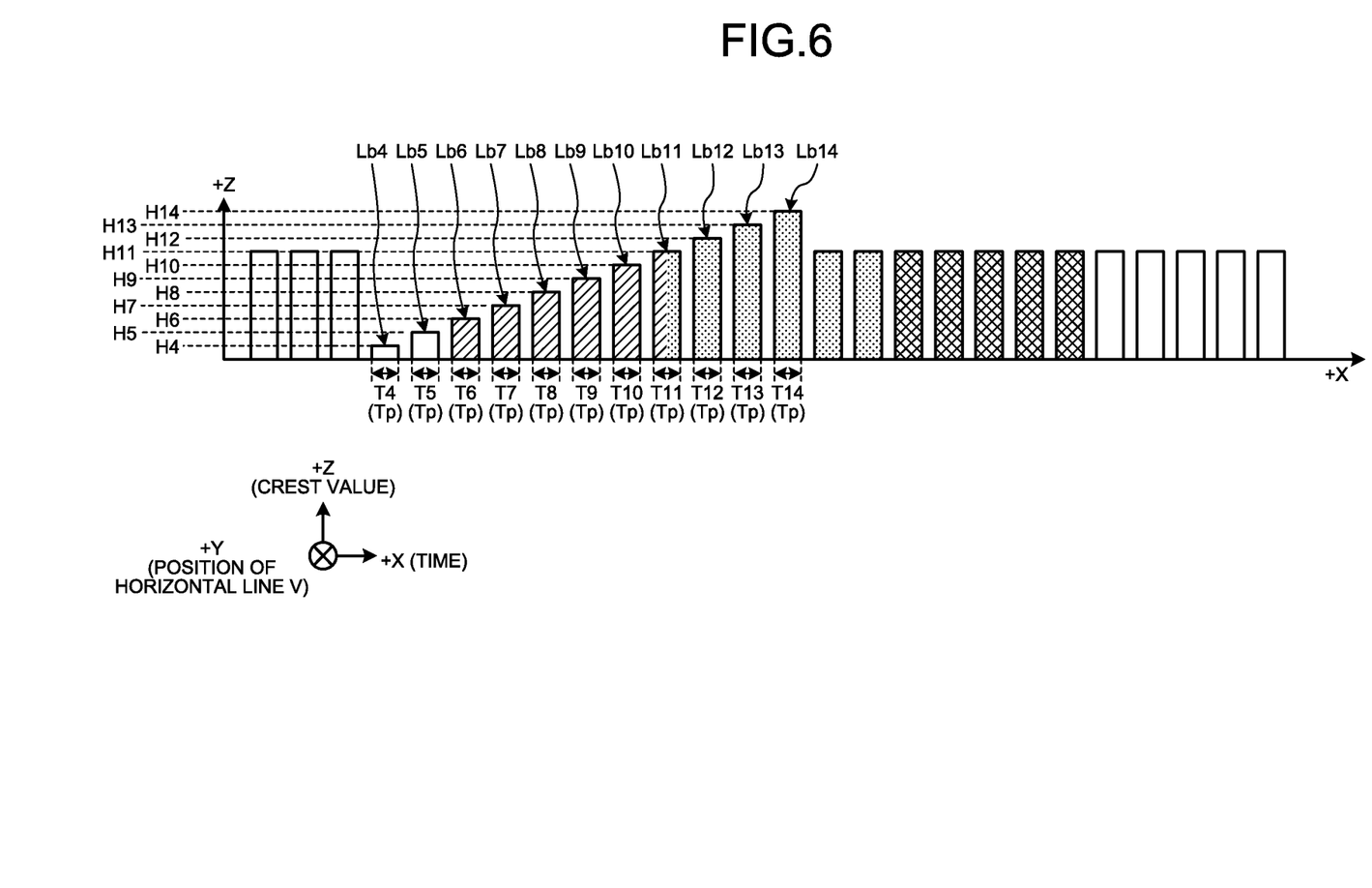
FIG. 6 is a diagram for explaining an exposure amount when light modulation control is executed.
Figure 7:
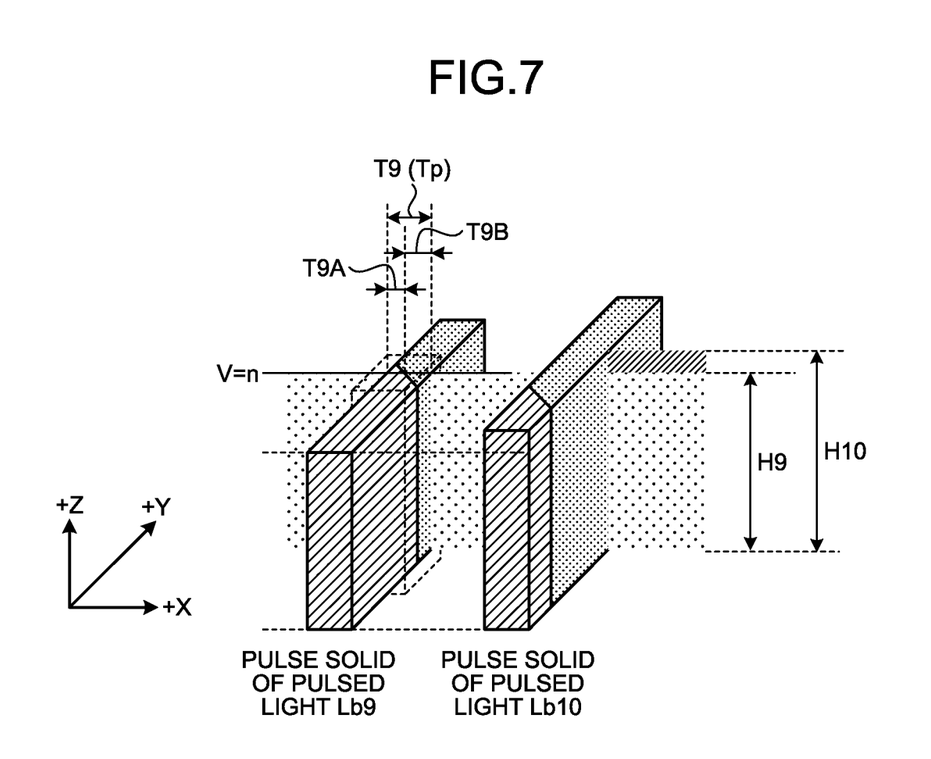
FIG. 7 is a diagram for explaining an exposure amount when light modulation control is executed.

FIGS. 6 and 7 are diagrams for explaining an exposure amount when light modulation control is executed. Specifically, FIG. 6 is a diagram when (b) of FIG. 3 is viewed from the −Y axis direction. FIG. 7 is a perspective view in which each of the pulse solids of the pulsed lights Lb9 and Lb10 illustrated in (b) of FIG. 3 is extracted and viewed from the −Y axis side.

Next, a case where the light source controller 471 executes light modulation control will be described. In the first embodiment, the light source controller 471 executes light modulation control of pulsed light, as illustrated in (b) of FIG. 3, FIG. 6 and FIG. 7, without changing pulse widths (illumination periods) of a pulsed current supplied to the light source 461 to make them all identical illumination period Tp and with changes in crest values of the pulsed current. The light modulation control is, for example, control for changing a crest value of a pulsed current based on a luminance average value of a specific area in an image based on a display image signal generated by the display controller 45, so as to make brightness of the image as a reference.

Hereinafter, a method for generating pixel signals of overlapping lines constituting pseudo pixel signals and a method for generating pixel signals of non-overlapping lines constituting pseudo pixel signals will be described in order.

First, the method for generating pixel signals of overlapping lines constituting pseudo pixel signals will be described.

When generating pseudo pixel signals, the image processing unit 44 uses, for an overlapping line, as described in the "case of no light modulation control" described above, a pixel signal obtained by synthesizing the first and the second corresponding pixel signals.

In other words, the image processing unit 44 makes the pixel signal of the horizontal line n, which is an overlapping line constituting the pseudo pixel signal with the pulsed light Lb9, a pixel signal obtained by synthesizing the first corresponding pixel signal calculated by formula (1) and the second corresponding pixel signal calculated by formula (2).

Here, when the light source controller 471 executes light modulation control, the illumination periods T4 to T14 each are uniformly "Tp", but the crest values H4 to H14 each have different values. More specifically, the exposure amounts of the pulsed lights Lb4 to Lb14 (each cross-sectional area (see FIG. 7) obtained by cutting each of the pulse solids of the pulsed lights Lb4 to Lb14 along the XZ plane (represented by dots in FIG. 7)) are different.

Consequently, when the light source controller 471 executes light modulation control, formula (1) may not be developed as formula (3). Similarly, formula (2) may not be developed as formula (4).

In other words, when the light source controller 471 executes light modulation control, as illustrated in formulae (1) and (2), it is necessary in calculating the first and the second corresponding pixel signals to consider parameters of both crest value and time (illumination period).

Next, the method for generating pixel signals of non-overlapping lines constituting pseudo pixel signals will be described.

When generating pseudo pixel signals, the image processing unit 44 uses, for a non-overlapping line, as described in the "case of no light modulation control" described above, a pixel signal obtained by multiplying a pixel signal for a specific one frame from each pixel of the non-overlapping line by a ratio of an amount of exposure made during a target illumination period within the specific one frame to a total exposure amount obtained by adding each exposure amount of all pulsed lights exposing the non-overlapping line within the specific one frame including the target illumination period.

In brief, the image processing unit 44 calculates the pixel signal of the horizontal line t, which is a non-overlapping line constituting the pseudo pixel signal with the pulsed light Lb9, by formula (5).

Here, when the light source controller 471 executes light modulation control, the illumination periods T6 to T10 each are uniformly "Tp", but the crest values H6 to H10 are different values. In other words, the exposure amounts of the pulsed lights Lb6 to Lb10 (each cross-sectional area (see FIG. 7) obtained by cutting each of the pulse solids of the pulsed lights Lb6 to Lb10 along the XZ plane (represented by dots in FIG. 7)) are different.

Thus, when the light source controller 471 executes light modulation control, formula (5) may not be developed as formula (6).

More specifically, when the light source controller 471 executes light modulation control, as indicated in formula (5), it is necessary in calculating a pixel signal of a non-overlapping line constituting a pseudo pixel signal to consider parameters of both crest value and time (illumination period).

According to the first embodiment described above, effects described below are obtained.

The control device 4 according to the first embodiment generates a pseudo pixel signal in consideration of parameters of both crest value and time (illumination period) (see formulae (1), (2), and (5)). Therefore, even when light modulation control is executed, an appropriate pseudo pixel signal may be generated. In other words, since it is possible to suppress fluctuations in brightness other than ones targeted by light modulation, variations in brightness within one frame or between consecutive frames may be reduced, and an image suitable for observation may be generated.

Further, the control device 4 according to the first embodiment modulates pulsed light by changing only a crest value without changing a pulse width of a pulsed current.

Thus, it is necessary to emit pulsed light with a very short pulse width of a pulsed current, and even when it is difficult to modulate pulsed light by changing the pulse width, pulsed light may be modulated favorably by changing a crest value.

Second Embodiment

Next, a second embodiment will be described.

In descriptions below, configurations similar to ones of the first embodiment described above are given identical numerals, and detailed descriptions thereof will be omitted or simplified.

In the first embodiment described above, the image sensor 262 includes a CMOS image sensor that generates a pixel signal by the rolling shutter system.

On the other hand, in the second embodiment, the image sensor 262 includes a CCD image sensor that generates a pixel signal by a global shutter system.

Figure 8:
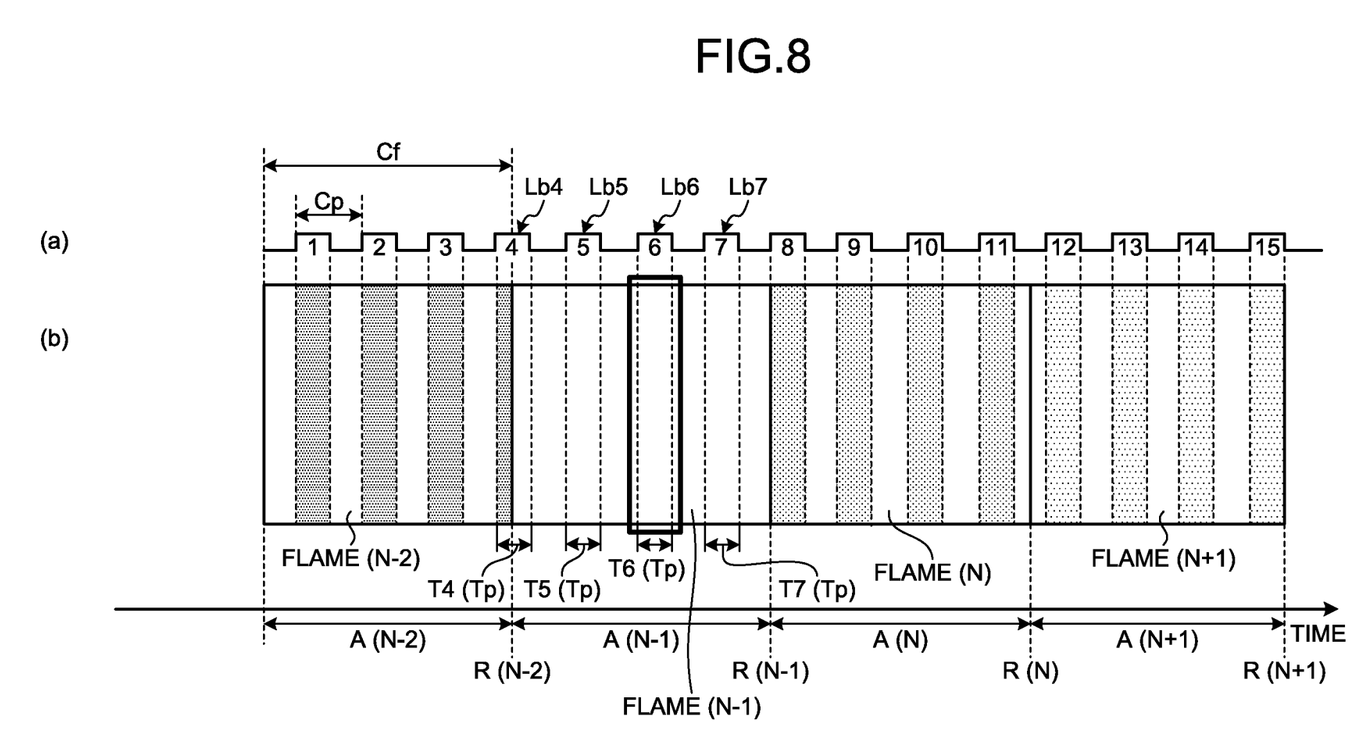
FIG. 8 is a time chart illustrating an emitting timing of pulsed light and an exposure and a reading timing by a reading unit according to a second embodiment.

FIG. 8 is a time chart illustrating an emitting timing of pulsed light and an exposure and a reading timings by the reading unit 264 in the second embodiment. Specifically, (a) of FIG. 8 is a timing chart illustrating an emitting timing of pulsed light emitted from the light source 461. (b) of FIG. 8 is a timing chart illustrating exposure and reading timings for a plurality of pixels by the reading unit 264.

Under the control of the imaging controller 472, the imaging unit 26 has, if in an identical frame, all pixels exposed in an identical period and read at an identical timing. More specifically, if in the frame (N−2), after exposure in an exposure period A (N−2), at time R (N−2), the pixel signal D (N−2) corresponding to the pixel signals of all pixels are read. Similarly, in the frames (N−1), (N), and (N+1), after exposure during exposure periods A (N−1), A (N), and A (N+1), at times R (N−1), R (N), and R (N+1), respectively, pixel signals D (N−1), D (N), and D (N+1) corresponding to the pixel signals of all pixels are read.

The light source 461 emits, under the control of the light source controller 471, as illustrated in (a) of FIG. 8, pulsed light for each light emission period Cp shorter than the frame period Cf of the image sensor 242.

In the second embodiment, the image processing unit 44 generates pseudo pixel signals with pulsed lights in which all horizontal lines V are non-overlapping lines among all pulsed lights. Further, when generating the pseudo pixel signals, the image processing unit 44 uses pixel signals obtained by multiplying pixel signals for a specific one frame from each pixel of a horizontal line V by a ratio of an amount of exposure made during a target illumination period within the specific one frame to a total exposure amount obtained by adding each exposure amount of all pulsed lights exposing the horizontal line V within the specific one frame including the target illumination period.

More specifically, a case of generating pseudo pixel signals with the pulsed light Lb6 will be described as an example.

The image processing unit 44 generates a pseudo pixel signal based on a pixel signal of each horizontal line V constituting the pixel signal D (N−1) of the frame (N −1) read at a next reading timing of the illumination period (target illumination period) of the pulsed light Ld6.

Here, in the exposure period of the frame (N−1), in addition to the illumination period T6 of the pulsed light Ld6, a latter half of the illumination period T4 of the pulsed light Ld4 and the illumination periods T5 and T7 of the pulsed lights Ld5 and Ld7 are also included.

Therefore, the pixel signal of the horizontal line V constituting the pseudo pixel signal with the pulsed light Lb6 is calculated by formula (7) below, as in the case of the non-overlapping line described in the first embodiment. In formula (7), H4 to H7 are crest values of pulsed currents for emitting the pulsed lights Lb4 to Lb7, respectively. The period T4B is a period including the illumination period T4 of the pulsed light Lb4 in the frame (N−1).

$$\text{pixel signal of horizontal line } V \text{ constituting} \quad (7)$$
$$\text{pseudo pixel signal with pulsed light } Lb6 =$$
$$\frac{H6*T6}{H4*T4B + H5*T5 + H6*T6 + H7*T7} *$$
$$(\text{pixel signal of horizontal line } V \text{ of pixel signals } D \ (N-1))$$

In the second embodiment, the image processing unit 44 generates, for each display cycle of the display device 5, one pseudo pixel signal with one pulsed light in which all horizontal lines V are non-overlapping lines, among all pulsed lights included in the display cycle. Then, the display controller 45 generates, for each display cycle, one display image signal from the one pseudo pixel signal.

The image processing unit 44 may generate, for each display cycle of the display device 5, pseudo pixel signals with a plurality of pulsed lights among all pulsed lights included in the display cycle. At this time, the display controller 45 generates, for each display cycle, one display image signal from the pseudo pixel signals.

Even when the image sensor 262 includes a CCD image sensor as in the second embodiment described above, effects similar to ones of the first embodiment described above may be obtained.

Other Embodiments

So far, the embodiments for carrying out the present disclosure have been described, but the present disclosure should not be limited by the embodiments described above.

In the first and the second embodiments described above, the endoscope 2 includes, but not limited to, a flexible endoscope but may include a rigid endoscope.

In the first and the second embodiments described above, in light modulation control, only a crest value is changed without changing a pulse width of a pulsed current. However, the present disclosure is not limited thereto and may adopt a configuration for modulating pulsed light by changing both pulse width and crest value.

According to a medical control device and an endoscope system according to the present disclosure, an image suitable for observation may be generated.

Although the disclosure has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. A medical control device comprising:
   light source control circuitry configured to
   control a light source to emit a plurality of pulses, each pulse having a pulse width and a crest value, in one frame of an image sensor, the image sensor including a plurality of pixels configured to receive light from an object illuminated with the plurality of pulses and generate pixel signals, the light source control circuitry configured to set different crest values for at least two pulses of the plurality of pulses based on a reference value in accordance with an image output from the image sensor;
   imaging control circuitry configured to control the image sensor to sequentially generate a pixel signal for each of the pixels within the one frame; and
   an image processor configured to generate, from the pixel signal, a pseudo pixel signal for a horizontal line among horizontal lines of the pixels, by multiplying a pixel signal generated during an illumination period of a light pulse of the plurality of pulses within the one frame from each pixel of the horizontal line by a ratio of an exposure amount of the light pulse for that horizontal line made in within the one frame to a total exposure amount obtained by adding each exposure amount of all light pulses of the plurality of pulses exposing the horizontal line during an exposure period,
   wherein each exposure amount for each light pulse within the exposure period is a value defined by the pulse width and the crest value.

2. The medical control device according to claim 1, wherein the horizontal line is a non-overlapping line for which the illumination period of the light pulse does not overlap a reading timing.

3. The medical control device according to claim 2, wherein
   the image processor is configured to use, when generating the pseudo pixel signal, for a horizontal line is an overlapping line in which the illumination period of the light pulse overlaps the reading timing, a pixel signal obtained by synthesizing a first corresponding pixel signal derived from a first pixel signal that is the pixel signal of a first frame read from the overlapping line at the reading timing that serves as a first reading timing and a second corresponding pixel signal derived from a second pixel signal that is the pixel signal of a second frame read from the overlapping line at a second reading timing, wherein one of the first frame and the second frame is the one frame,
   the first corresponding pixel signal is a pixel signal obtained by multiplying the first pixel signal by a ratio of the exposure amount of the light pulse made in the first frame to a total exposure amount obtained by adding each exposure amount of all light pulses of the plurality of pulses exposing the overlapping line within the first frame, and
   the second corresponding pixel signal is a pixel signal obtained by multiplying the second pixel signal by a ratio of the exposure amount of the light pulse made in the second frame to a total exposure amount obtained by adding each exposure amount of all light pulses of the plurality of pulses exposing the overlapping line within the second frame.

4. The medical control device according to claim 1, wherein the light source control circuitry is configured to modulate the plurality of pulses by changing the crest value without changing the pulse width of the pulsed current.

5. An endoscope system comprising:
   a light source configured to emit pulsed light according to a pulsed current;
   an image sensor including a plurality of pixels configured to receive light from an object illuminated with the pulsed light and generate pixel signals; and
   the medical control device according to claim 1.

6. The endoscope system according to claim 5, wherein the image sensor is a CMOS image sensor.

7. The endoscope system according to claim 5, wherein the image sensor is a CCD image sensor.

8. The medical control device according to claim 1, wherein the reference value is a brightness of the image output by the image sensor.

9. The medical control device according to claim 1, wherein the reference value is a luminance average value of a specific area in the image output by the image sensor.

* * * * *